(12) United States Patent
Shimizu et al.

(10) Patent No.: US 10,359,402 B2
(45) Date of Patent: Jul. 23, 2019

(54) TWO-DIMENSIONAL LIQUID CHROMATOGRAPHIC ANALYZER AND ANALYTICAL METHOD

(71) Applicant: HITACHI HIGH-TECH SCIENCE CORPORATION, Minato-ku, Tokyo (JP)

(72) Inventors: Katsutoshi Shimizu, Tokyo (JP); Hideko Kanazawa, Sagamihara (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 386 days.

(21) Appl. No.: 15/081,103

(22) Filed: Mar. 25, 2016

(65) Prior Publication Data

US 2016/0282315 A1 Sep. 29, 2016

(30) Foreign Application Priority Data

Mar. 25, 2015 (JP) ................. 2015-080384

(51) Int. Cl.
*G01N 30/30* (2006.01)
*G01N 30/46* (2006.01)
*G01N 30/54* (2006.01)

(52) U.S. Cl.
CPC ........... *G01N 30/30* (2013.01); *G01N 30/463* (2013.01); *G01N 30/54* (2013.01); *G01N 2030/3007* (2013.01)

(58) Field of Classification Search
CPC ........ G01N 30/30; G01N 30/50; G01N 30/54; G01N 30/463; G01N 2030/3007; G01N 30/88; G01N 2030/8813; G01N 2030/8877; G01N 30/74; G01N 30/462

USPC ........... 73/23.35, 23.39, 23.41, 23.42, 61.52, 73/61.53, 61.55, 61.56, 61.57; 210/198.2, 210/656–659; 422/70, 89
See application file for complete search history.

(56) References Cited

U.S. PATENT DOCUMENTS

| | | | |
|---|---|---|---|
| 8,117,896 B2 * | 2/2012 | Lucas | G01N 30/08 73/23.41 |
| 2006/0228770 A1 | 10/2006 | Kanazawa | |
| 2007/0199874 A1 | 8/2007 | Ito et al. | |
| 2013/0134095 A1 * | 5/2013 | Anderer | B01D 15/1878 210/656 |

(Continued)

FOREIGN PATENT DOCUMENTS

JP  2008-96455 A   4/2008
JP  5362943 B2   12/2013

OTHER PUBLICATIONS

Office Action dated Jun. 5, 2019 for U.S. Appl. No. 16/267,929, 14 pgs.

*Primary Examiner* — Lisa M Caputo
*Assistant Examiner* — Suman K Nath
(74) *Attorney, Agent, or Firm* — Brinks Gilson & Lione

(57) ABSTRACT

A two-dimensional liquid chromatographic analyzer, in which a temperature control part changes a temperature in a single-step manner and switches the temperature at a high speed. Also, the temperature control part has a holder around a separation column so that the temperature of the separation column can be changed to a preset temperature. A first separation column thereof changes elution time(s) of the objective component(s) by temperature modulation and the mobile phase of the first separation column is an aqueous mobile phase having a constant composition.

3 Claims, 5 Drawing Sheets

(56) References Cited

U.S. PATENT DOCUMENTS

2016/0193546 A1* 7/2016 Shimizu .................. B01J 20/26
554/191

* cited by examiner

FIG. 4A  FIRST-DIMENSIONAL CHROMATOGRAM
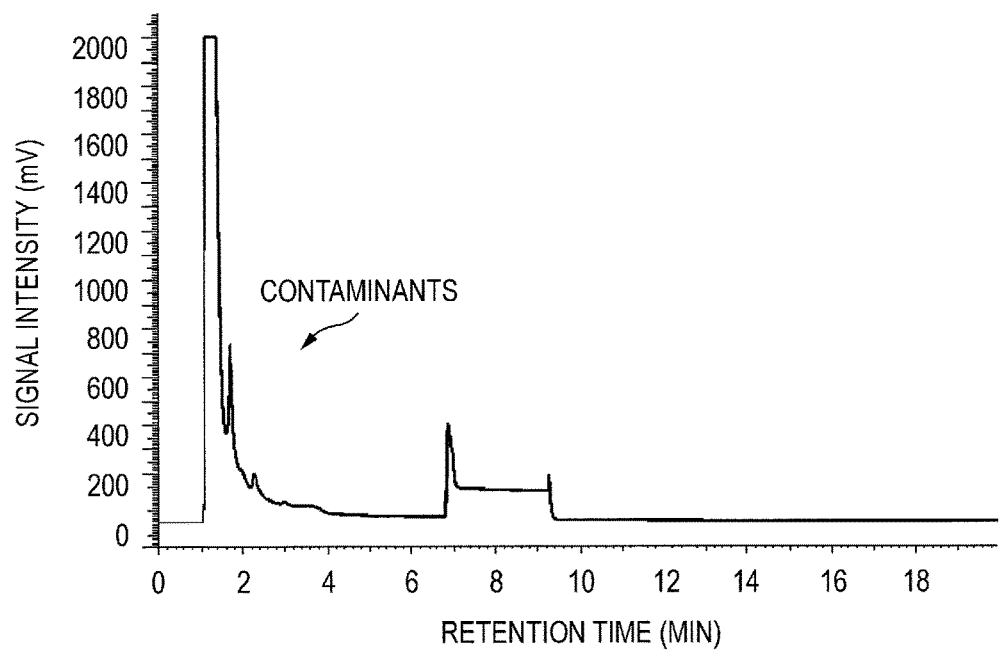
FIG. 4B  SECOND-DIMENSIONAL CHROMATOGRAM
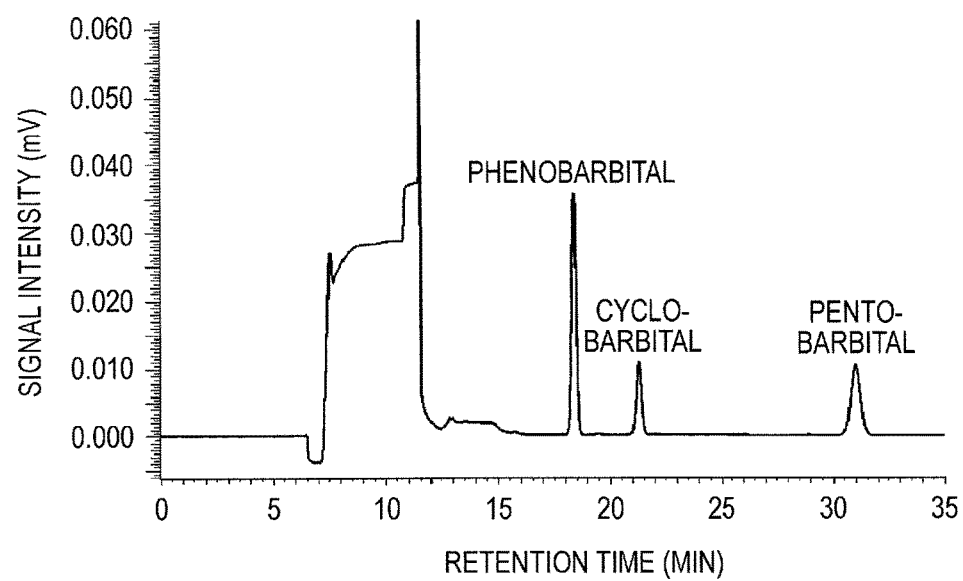

TWO-DIMENSIONAL LIQUID CHROMATOGRAPHIC ANALYZER AND ANALYTICAL METHOD

RELATED APPLICATIONS

This application claims priority under 35 U.S.C. § 1 19 to Japanese Patent Application Nos. 2015-080384 filed Mar. 25, 2015 and 2016-79130 filed Mar. 25, 2016. The entire contents of both of applications are hereby incorporated by reference.

BACKGROUND OF THE INVENTION

1. Field of the Invention

The disclosure relates to a liquid chromatograph. Specifically, the disclosure relates to a two-dimensional liquid chromatographic analyzer having a plurality of separation columns and an analytical method.

2. Description of the Related Art

A liquid chromatograph is an apparatus configured to separate objective components in a sample by a separation column while feeding a mobile phase and to detect the components that flow out in an order of their separation by a detector such as a spectrophotometer so as to analyze the components of the sample.

For the liquid chromatograph, separation columns of various separation modes such as an ion-exchange mode, a normal phase mode, and a reversed phase mode are employed for separating ionic components, hydrophilic components, hydrophobic components, and the like in samples and the kind of the mobile phase varies depending on the separation mode.

For the mobile phase, for improving separation and shortening analysis time, there is generally used gradient elution in which two or more kinds of mobile phases are fed while changing a mixing ratio thereof.

On the other hand, there is also known a method of achieving an improvement in separation and shortening of analysis time by changing the temperature of the separation column. For example, in a reversed phase chromatograph in which, as a representative reversed phase separation column, an octadecylsilyl (ODS) group is used as a functional group, it is generally known that elution is fastened when the temperature of the separation column becomes high.

Japanese Patent No. 5362943 reports a simple and convenient drug metabolizing ability evaluation system in which a filling agent whose surface is covered with a polymer having hydration force that changes within the temperature range of 0 to 80° C. is used for a separation column and objective components are separated and measured by controlling the temperature of the separation column.

However, in the case where components in a biological sample such as serum are analyzed using a liquid chromatograph, a plurality of components are present as a mixture in the biological sample, and use of one column may result in insufficient separation or may take a long period of time for analysis.

In Japanese Patent No. 5362943, after the biological sample is pre-treated using a column for solid-phase extraction, objective components are analyzed through a separation column.

As a specific separation method, there is used a two-dimensional liquid chromatographic analytical method in which, using a flow channel switching valve, columns of two kinds of different separation modes are combined and the objective components separated by a first (first-dimensional) separation column are fractionated and then introduced into a second (second-dimensional) column to further separate them.

In the two-dimensional liquid chromatography, it is common to perform analysis using an ion exchange column as the first-dimensional column and a reversed phase column as the second-dimensional one.

In the first-dimensional ion exchange column, the objective components are separated by salt concentration or pH of a buffer solution as a mobile phase and the separated objective components are introduced into the second-dimensional reversed phase column. In the second-dimensional reversed phase column, further separation is performed using a mobile phase containing an organic solvent.

JP-A-2008-96455 describes examples of the two-dimensional liquid chromatographic analyzer in which the first-dimensional separation and the second-dimensional separation are performed.

The technique described in JP-A-2008-96455 is that, in order to perform replacement of the mobile phase in the system efficiently, the components separated in the first dimension are once trapped and concentrated by a trap column and the components trapped by the trap column are further separated and analyzed in the second dimension. As a configuration thereof, there has been reported a two-dimensional liquid chromatograph capable of analyzing even any components using fewest three trap columns.

JP-A-2008-96455 describes a two-dimensional liquid chromatograph comprising a first-dimensional separation flow channel for introducing a sample injected from a sample injection part into a separation column with a mobile phase for separation to separate the sample, three trap columns, a flow channel of a mobile phase for analysis for supplying the mobile phase for analysis, a second-dimensional analytical flow channel for introducing the components trapped in the trap columns into an analytical column with the mobile phase for analysis to analyze the components, a flow channel of a mobile phase for desalination for supplying the mobile phase for desalination, and a flow channel switching mechanism for connecting the first-dimensional separation flow channel to one trap column, connecting the flow channel of the mobile phase for desalination to another one trap column, connecting the first-dimensional separation flow channel to still another one trap column, and also switching the connections of the trap columns and the flow channels, wherein the flow channel switching mechanism includes a first and second two-position valves to which one end and another end of each of the three trap columns are connected, a third two-position valve to which the first-dimensional separation flow channel, the flow channel of the mobile phase for desalination, and the flow channel of the mobile phase for analysis are connected and whose one end is connected to another end of three flow channels that are connected to the first two-position valve, and a fourth two-position valve whose one end is connected to another end of three flow channels that are connected to the second two-position valve and the second-dimensional analytical flow channel.

The flow channels are connected by valves so that the three trap columns can independently take action. By connecting the flow channels so as to perform concentration in one trap column, desalination in another one trap column, and elution in still another one trap column simultaneously, the concentration action, the desalination action, and the elution action simultaneously proceed in respective different trap columns by valves, so that it is possible to continue second-dimensional analysis with three trap columns without limiting the number of components.

SUMMARY OF THE INVENTION

In a common two-dimensional liquid chromatograph, a buffer solution is used as a mobile phase of a first-dimensional ion exchange column.

In the ion exchange column, a buffer solution is used as a mobile phase and objective components are separated by increasing ionic strength (salt concentration) of the buffer solution or changing pH thereof. Therefore, in the ion exchange column, there is used gradient elution in which two or more kinds of mobile phases are fed while changing a mixing ratio thereof.

A salt is precipitated by mixing the buffer solution and the organic solvent contained in the mobile phase of the second-dimensional reversed phase column and thus clogging is formed in a piping or the second-dimensional reversed phase column. In order to prevent the clogging, a trap column for feeding a mobile phase for desalination becomes necessary and there is a problem that system configuration is complicated by providing a switching valve for the trap column and the like.

The disclosure provides a two-dimensional liquid chromatographic analyzer and an analytical method, which are capable of performing high sensitive analysis of objective component(s) in a sample such as a biological one with a simple configuration in which a system for feeding a mobile phase for desalination is not needed by preventing the salt precipitation.

The two-dimensional liquid chromatograph of the invention may be configured as follows.

A two-dimensional liquid chromatographic analyzer comprising: a liquid feed part configured to feed a mobile phase; an injection part configured to inject a sample; a first separation column configured to separate and fractionate the sample containing a plurality of components; a second separation column configured to separate the fractionated components; a temperature control part configured to control temperature of each separation column; and a detection part configured to detect the separated components, wherein the temperature control part comprises a holder made of metal and configured to hold the first separation column so as to transmit a temperature change of the first temperature control part to the first separation column.

The first separation column may be a temperature-responsible gel modification column having a functional polymer layer whose surface nature is reversibly changed between hydrophilic nature and hydrophobic nature by temperature modulation or a reversed phase column to which it is possible to feed a 100% aqueous mobile phase, and the second separation column may be a reversed phase column.

In a two-dimensional liquid chromatographic analytical method, a mobile phase to be fed to a first separation column is an aqueous mobile phase, and the composition of the mobile phase to be fed to the first separation column is not changed at the separation and fractionation of objective components.

When the present analyzer is used, it becomes possible to analyze components of a biological sample or the like with a simple system.

By adopting a temperature-responsible gel modification separation column as a first-dimensional first separation column, it is possible to separate major contaminant components and a drug group in a biological sample such as serum with an aqueous mobile phase alone.

The temperature-responsible gel modification separation column can control elution time of a drug in the first-dimensional first separation column by temperature control. By using the temperature-responsible gel modification separation column, at the time when a plurality of drugs are simultaneously analyzed, the elution time of the drug group can be controlled by temperature modulation and thus any drug can be introduced into a second-dimensional second separation column.

The mobile phase of the first-dimensional first separation column is an aqueous mobile phase having a constant composition and it is not necessary to use a buffer solution from which a salt may be precipitated through mixing with a mobile phase of the second separation column containing an organic solvent at the introduction into the second-dimensional column. Therefore, it is unnecessary to feed a mobile phase for desalination and a trap column and a switching valve become unnecessary, so that system configuration becomes simple. The simple system configuration also improves operability and maintainability.

Next, the aqueous mobile phase is introduced into the second-dimensional second separation column together with objective component(s). The second separation column is a reversed phase column and the objective component(s) does not immediately elute from the second-dimensional second separation column and remain in the second separation column.

For the mobile phase of the second separation column, gradient elution with an organic solvent and an aqueous mobile phase is used.

The objective component(s) remaining in the second separation column is once converged in the column and is eluted with the organic solvent contained in the mobile phase of the second separation column, so that the peak(s) of the eluted objective component(s) is sharply detected.

Thereby, in the second-dimensional chromatogram, the peak(s) of the objective component(s) becomes sharp and thus high sensitivity analysis is possible.

BRIEF DESCRIPTION OF THE DRAWINGS

FIGS. 4A and 4B are chromatograms obtained by analyzing drugs in serum by a liquid chromatographic analyzer, in which FIG. 4A shows a first-dimensional chromatogram and FIG. 4B shows a second-dimensional chromatogram.

DETAILED DESCRIPTION OF THE PREFERRED EMBODIMENTS

The following will describe embodiments of the invention with reference to the drawings.

Figure 1A:
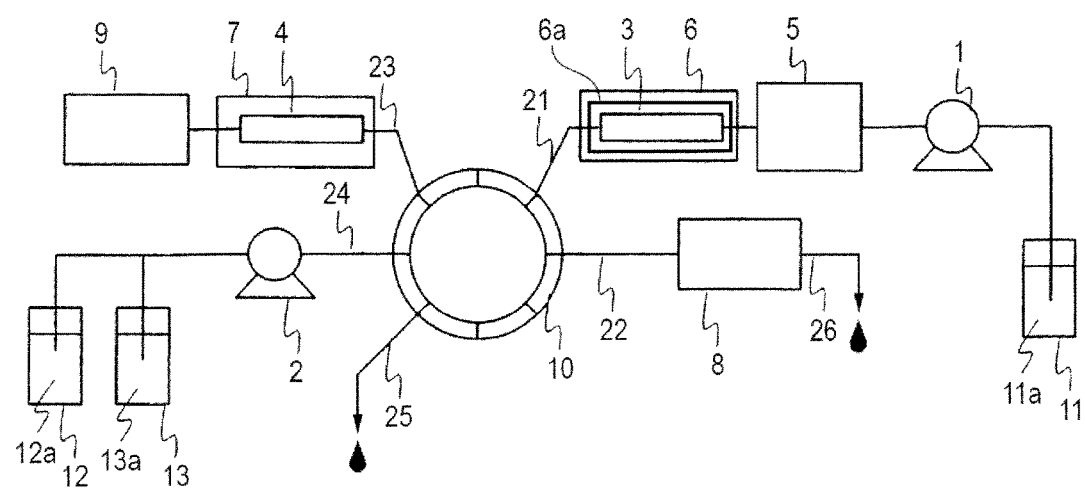
FIG. 1A is an outline block diagram of a liquid chromatographic analyzer.

FIG. 1A is an outline block diagram of a two-dimensional liquid chromatographic analyzer that is the first embodiment of the invention.

The two-dimensional liquid chromatographic analyzer comprises pumps 1 and 2 for feeding eluents, a sample injection device 5 for injecting a sample into the system, separation columns 3 and 4 for separating the sample sent to the system, temperature control parts 6 and 7 for controlling temperatures of separation columns, detectors 8 and 9 for detecting sample components separated by the separation columns 3 and 4, and a valve 10 for connecting/separating individual flow channels.

In the two-dimensional liquid chromatographic analyzer, a pump 1 feeds an eluent A 11*a* from an eluent container 11 to the sample injection device 5. The pump and the eluent container functioning as a liquid feed part. The sample injection device 5 injects a sample into a flow channel together with the eluent A 11 *a* from the pump 1.

The components in the sample injected into the flow channel are sent to the separation column (first separation column) 3 and are eluted into a flow channel 21 in an ascending order of interaction with the separation column 3.

The separation columns 3 and 4 are controlled to preset temperatures suitable for separation by the temperature control parts 6 and 7, respectively.

The components in the sample eluted into the flow channel 21 are sent to the detector 8 through a six-way valve 10 and a flow channel 22 and contaminant components alone are discharged from a flow channel 26 as a waste solution. When the separation of the contaminant components is completed, the flow channel 21 from the separation column 3 is connected to a flow channel 23 though the six-way valve 10. At this time, eluents B (12*a* and 13*a*) are fed from eluent containers 12 and 13 to the flow channel 23 by a pump 2 through a flow channel 24 and the six-way valve 10, and are fed to the separation column (second separation column) 4 together with the eluent A 11*a* containing the sample from the separation column 3.

The components separated by the separation column 4 are eluted in an ascending order of interaction with the separation column 4 and measurement of each component is performed on a detector 9.

The timing of switching the path of the flow channel 21 to the flow channel 22 to the path of the flow channel 21 to the flow channel 23 by the six-way valve 10 is decided through determination of the elution time of the contaminant components previously and, at measurement, the switching of the flow channels is set based on the time.

The eluents B (12*a* and 13*a*) are fed by the pump 2 but, during time periods other than the time period where the flow channel 21 and the flow channel 23 are connected for feeding the sample solution from the separation column 3 to the separation column 4, are discharged as a waste solution while the flow channel 24 and a flow channel 25 are connected by the six-way valve 10.

Figure 1B:
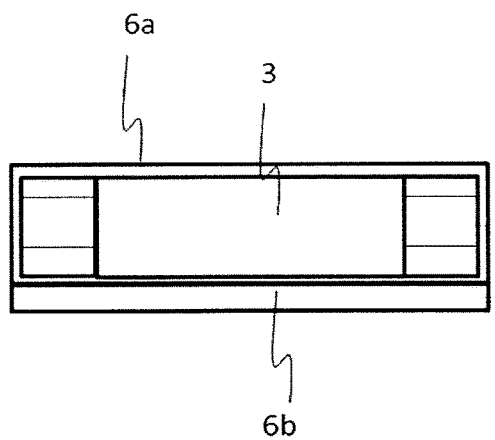
FIG. 1B is a structural drawing of a temperature control part.

The separation columns 3 and 4 are placed in the temperature control parts 6 and 7, respectively. The temperature control part 6 of the separation column 3 is configured to switch a temperature of the separation column 3 to a target temperature. The temperature control part 6 has a holder 6*a* around the separation column 3 so as to hold that the separation column 3. The holder 6*a* is made of metal such as aluminum alloy, copper alloy, etc., excellent in thermal conductivity. As shown by FIG. 1B, an inner structure of the holder 6*a* is formed to fit an outer structure of the separation column 3, so that the holder 6*a* is close contactable with an outer circumference of the separation column 3 so as to surround the outer circumference of the separation column 3. According thereto, temperature change of the temperature control part 6 can be efficiently transmitted to the separation column 3.

The temperature control part 6 is configured to change the temperature of the separation column 3 from a first temperature to a second temperature in a single-step manner (e.g., in a steep manner) and switch the temperature of the separation column 3 at a high speed to reach a new target temperature.

As the separation column 3, there is employed a temperature-responsible gel modification column having a polymer layer of a polyN-isopropylacrylamide (PNIPAAm) layer and butyl methacrylate (BMA) as a hydrophobic comonomer introduced into the PNIPAAm chains on surfaces of silica gel beads using a gel modification method.

On the surface of the polymer layer of the temperature-responsible gel modification column of the separation column 3, a change between hydrophilic nature and hydrophobic nature occurs through a change in the structure of the polymer chain on the surface caused by temperature change.

In the separation column 3, by means of the temperature control part 6, the hydrophilic and hydrophobic characteristics change through the change in the structure of the polymer chain on the polymer layer surface of the temperature-responsible gel modification column, and the separation column 3 is set at a temperature suitable for the separation of the objective component(s) by the interaction with the eluent.

The temperature control part 6 is provided with a heat block 6*b* as a heat source. Temperature of the heat block 6*b* is controlled by a Peltier element. The temperature control part 6 is configured to control the temperature of the separation column 3 by directly transmitting the temperature of the heat block 6*b* to the holder 6*a* so as to change the temperature of the separation column 3 to reach the set temperature within a short time.

Figure 5:
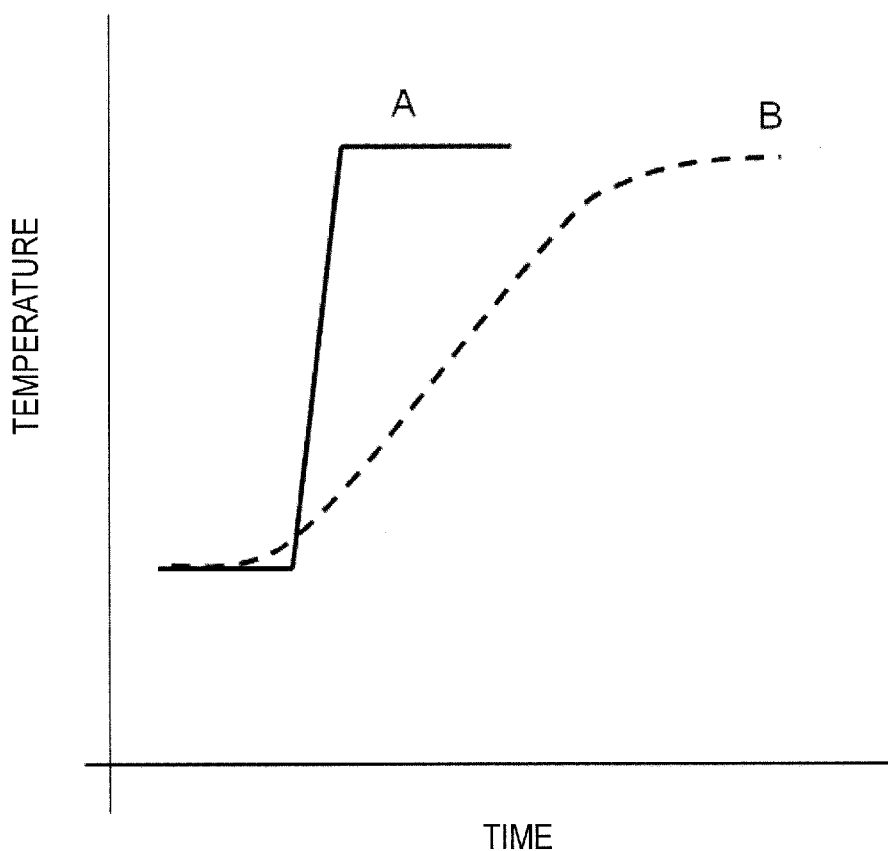
FIG. 5 shows temperature curves when being changed from one set temperature to another set temperature.

In a related-art liquid chromatograph, temperature change when being switched from one set temperature to new set temperature, the temperature increases as shown by a curved line B in FIG. 5, so that transient becomes long. In such a related-art liquid chromatograph, in order to maintain reproducibility of a retention time, it becomes necessary to perform the analysis after waiting for several times until the temperature becomes stable at the new set temperature. On the other hand, the temperature control part 6 can change the temperature steeply as shown by a curved line A in FIG. 5, so that transient can be made short and temperature can become stable at the new set temperature quickly. The temperature control part 6 can change the temperature from a room temperature to 40° C. within about four minutes. Incidentally, temperature range that can be set by the temperature control part 6 is not limited thereto.

Alternatively, the temperature of the separation column 3 is set or modulated by the temperature control part 6 so that suitable temperature modulation is performed for adsorbing a specific substance in a measuring sample onto the polymer layer surface of the temperature-responsible gel modification column and, after a certain period of time, releasing the specific substance by modulating the temperature to change the characteristics of the polymer layer surface of the temperature-responsible gel modification column.

Figure 2:
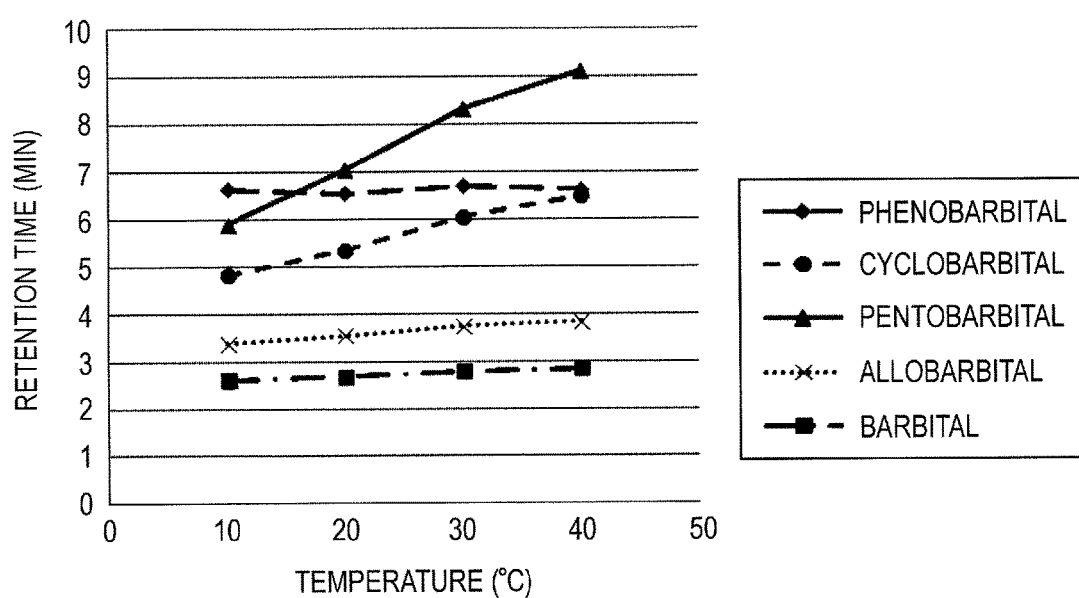
FIG. 2 is a graph showing a relationship between temperature preset and elution time.

FIG. 2 shows retention times of barbital-based drugs in the case where the temperature of the separation column 3 is modulated. The surface of the polymer layer of the temperature-responsible gel modification column is changed from hydrophobic nature to hydrophilic nature by changing the temperature of the separation column 3 from a high temperature to a low temperature at an arbitrary time and thereby it is possible to change the retention time(s) of the objective component(s) to achieve separation and fractionation.

The separation column 4 is a reversed phase separation column that is employed in a reversed phase chromatography in which an octadecylsilyl (ODS) group is used as a representative.

The eluents B (12a and 13a) to be fed to the separation column 4 may contain the eluent A 11a or the eluent A 11a and an organic solvent (methanol, acetonitrile, tetrahydrofuran, or the like to be commonly used in a liquid chromatograph) contained therein. Moreover, the eluents B (12a and 13a) to be fed to the separation column 4 may not have a constant composition, and gradient elution may be performed in which the composition is changed, depending on the analysis time.

The reversed phase column achieves separation by hydrophobic interaction between an objective component and an eluent. More specifically, the elution time of the objective component is shortened when the ratio of the organic solvent in the eluent increases, while the objective component remains in the reversed phase column and is concentrated when the ratio of the organic solvent in the eluent decreases.

The separation column 4 is connected to the six-way valve 10 and the components eluted from the separation column 3 are supplied together with the eluent A 11a at regular intervals.

The eluent A 11a to be fed to the separation column 3 is an aqueous mobile phase.

The components supplied to the separation column 4 remain in the separation column 4 and are concentrated since the eluent A 11a is an aqueous mobile phase.

After the components eluted from the separation column 3 are supplied to the separation column 4 together with the eluent A 11a, the six-way valve 10 is switched and the eluents B (12a and 13a) are supplied to the separation column 4.

The eluents B (12a and 13a) contain an organic solvent. Since the objective component(s) concentrated in the separation column 4 is promptly eluted by the eluents B (12a and 13a) containing the organic solvent after the switching of the six-way valve 10, the peak(s) to be detected becomes sharper.

Figure 3:
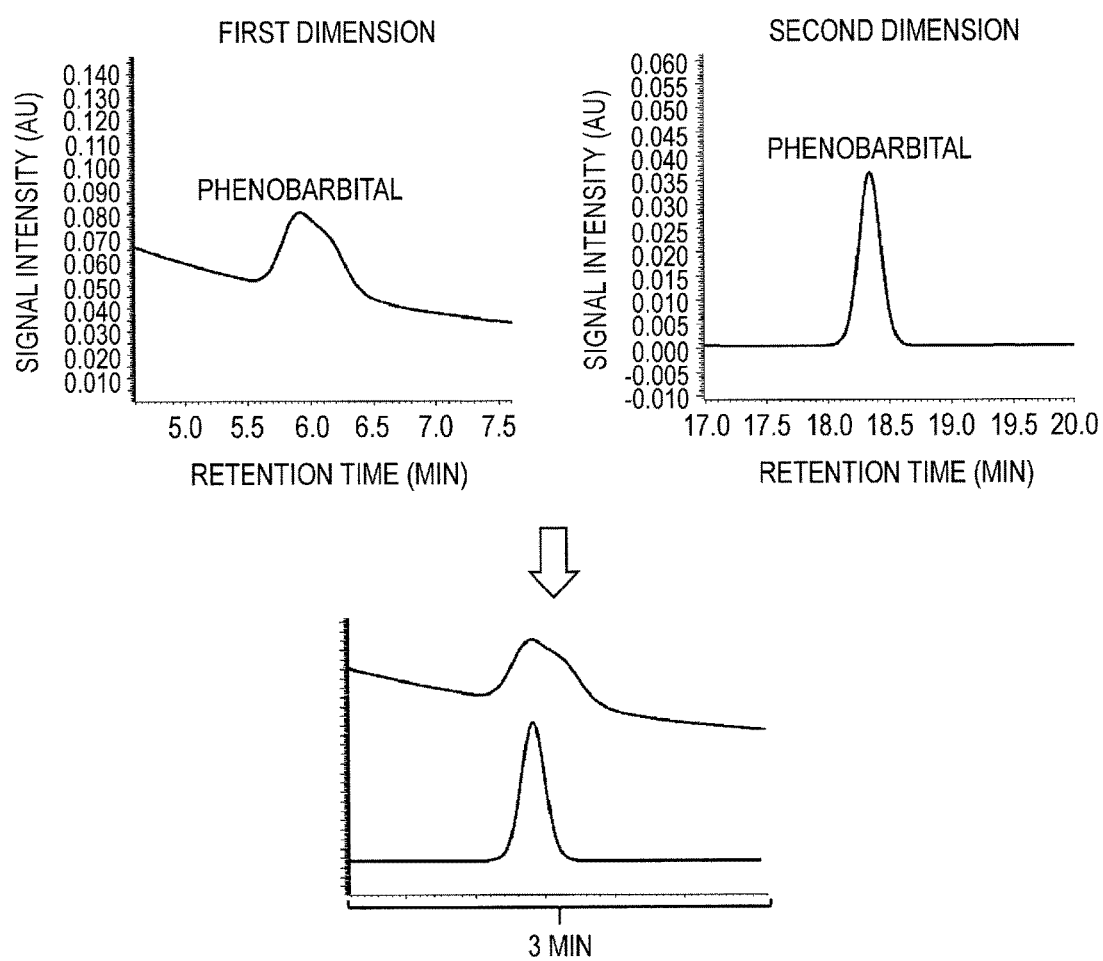
FIG. 3 is a chromatogram showing a concentration effect by a liquid chromatographic analyzer.

FIG. 3 is a chromatogram showing a concentration effect by a liquid chromatographic analyzer. The peak separated in the first-dimensional separation column becomes sharper in the second-dimensional separation column owing to the concentration effect.

On the other hand, the eluent A 11a is an aqueous solvent having a constant composition and the eluents B (12a and 13a) are solvents of the eluent A 11a or the eluent A 11a and an organic solvent contained therein. The eluent A 11a does not precipitate a salt in a piping or the separation column 4 of the liquid chromatographic analyzer when the eluent comes into contact with the eluents B (12a and 13a) after the switching of the six-way valve 10.

FIGS. 4A and 4B are chromatograms obtained by analyzing a serum containing phenobarbital, cyclobarbital, and pentobarbital as a sample by the liquid chromatographic analyzer and analytical method shown in Example. As for the sample directly injected, proteins that are contaminants are removed in the first dimension and clear separation of the drugs is performed in the second dimension.

Measurement Conditions

Sample: A tetrahydrofuran solution of phenobarbital, cyclobarbital, and pentobarbital that are psychoactive drugs was used as an authentic sample.

The authentic sample was dried to solidness under nitrogen and re-dissolved in a freeze-dry pooled serum and the resulting one was used as a sample.

<First Dimension>

Pre-treatment column: P(NIPAAm-co-BMA 5%) gel modification column (4.6 mm I.D.×150 mm L)

Mobile phase: 10 mM ammonium acetate (pH 6.5)

Flow rate: 1.0 mL/min

Detection wavelength: 220 nm

Injection amount: 10 µL

<Second Dimension>

Separation column: LaChrom IIC18 (5 µm) (4.6 mm I.D.×150 mm L)

Mobile phase: acetonitrile/10 mM ammonium acetate (pH 6.5)=75/25 (v/v)

Flow rate: 1.0 mL/min

Detection wavelength: 200 to 400 nm

Switching time: 5.5 to 9.2 min

In the disclosure, a temperature-responsible gel modification column is used as a separation column 3 but the separation column is not limited thereto. The other portions are also not limited to the aforementioned embodiments and can be appropriately modified or improved. The material, shape, size, numerical values, form, number, arrangement, and the like of each constituting element in the aforementioned embodiments are arbitrary and are not limited as far as they can achieve the invention.

What is claimed is:

1. A two-dimensional liquid chromatographic analyzer comprising:
    a liquid feed part configured to feed a mobile phase;
    an injection part configured to inject a sample;
    a first separation column configured to separate and fractionate the sample containing a plurality of components;
    a second separation column configured to separate the fractionated components;
    a first temperature control part configured to control temperature of the first separation column;
    a second temperature control part configured to control temperature of the second separation column;
    a detection part configured to detect the separated components,
    wherein the first temperature control part comprises a holder made of metal and configured to hold the first separation column so as to transmit a temperature change of the first temperature control part to the first separation column,
    wherein the first separation column is a temperature-responsible gel modification separation column having a functional polymer layer whose surface nature is reversibly changed between hydrophilic nature and hydrophobic nature by temperature modulation.

2. The two-dimensional liquid chromatographic analyzer according to claim 1, wherein the first temperature control part is configured to change the temperature of the first separation column from a first temperature to a second temperature in a single step with respect to time and switch the temperature of the first separation column by directly transmitting the temperature to the holder.

3. The two-dimensional liquid chromatographic analyzer according to claim 1, wherein the second separation column comprises a reversed phase column including an octadecylsilyl (ODS) column.

* * * * *